United States Patent [19]

Buehler et al.

[11] Patent Number: 5,137,732
[45] Date of Patent: Aug. 11, 1992

[54] RIBOFLAVIN GRANULES CONTAINING NO INACTIVE INGREDIENT

[75] Inventors: Volker Buehler, Wachenheim; Hermann Petersen, Gruenstadt, both of Fed. Rep. of Germany

[73] Assignee: BASF Aktiengesellschaft, Ludwigshafen, Fed. Rep. of Germany

[21] Appl. No.: 567,732

[22] Filed: Aug. 15, 1990

[30] Foreign Application Priority Data

Aug. 23, 1989 [DE] Fed. Rep. of Germany ....... 3927810

[51] Int. Cl.$^5$ .............................. A61U 9/14
[52] U.S. Cl. ................... 424/489; 424/474; 424/490; 514/904; 514/905
[58] Field of Search ........ 424/474, 489, 490; 514/904, 905

[56] References Cited

U.S. PATENT DOCUMENTS 4,619,829 10/1986 Motschan ........................... 424/128

FOREIGN PATENT DOCUMENTS 0219276 4/1987 European Pat. Off. .
0307767 7/1988 European Pat. Off. .
0345717 6/1989 European Pat. Off. .

OTHER PUBLICATIONS

Connine and Hadley, Small Solid Pharmaceutical Spheres, D+C.I., Apr. 1970, p. 38.
Wissenschaftliche Verlagsgesellschaft, pp. 98–99, V. Buhler, "Vademecum for Vitamin Formulations".
P. H. List: "Arzneiformenlehre", Ein Lehrbuch fur Pharmazeuten Dr.rer.nat. Paul Heinz List, Wiss. Verlagsges. Stuttgart, DE 1976, pp. 19–20.
R. Voight, "Lehrbuch der pharmazeutischen Technologie", 1976, p. 163, Verlag Chemie, Berlin, DE, p. 163, 8.3.2.2.

Primary Examiner—Thurman K. Page
Assistant Examiner—Louis A. Piccone
Attorney, Agent, or Firm—Oblon, Spivak, McClelland, Maier & Neustadt

[57] ABSTRACT

Riboflavin granules contain no inactive ingredient and have a mean particle diameter of from 50 to 1,000 μm are produced as described and used for preparing drugs and human and animal foods.

2 Claims, No Drawings

RIBOFLAVIN GRANULES CONTAINING NO INACTIVE INGREDIENT

The present invention relates to riboflavin granules which contain no inactive ingredient and whose mean particle diameter is 50–1,000 μm, to a process for producing these granules, and to the use thereof for preparing riboflavin-containing drugs and human and animal foods, in particular tablets.

Riboflavin (vitamin B2) is, when produced by synthesis or biotechnologically, in the form of powders containing very fine crystalline particles with a mean maximum diameter of about 20 μm.

Since this powder is highly dusting, has a very low bulk density, usually below 0.2 g/ml, picks up electrostatic charges and flows only very poorly, its further processing is possible only with great difficulty. In particular, it is unsuitable for producing tablets with a riboflavin content exceeding 25% by weight (V. Bühler, "Vademecum for Vitamin Formulations", Wissenschaftliche Verlagsgesellschaft, Stuttgart, pages 98–99).

This is why riboflavin is marketed in the form of granules produced using a binder (see, for example, EP-A 219 276).

Although these granules are very suitable for further industrial processing, whether direct tabletting or preparing other riboflavin-containing drug products or human and animal foods containing vitamin B2, they are often unsatisfactory because they are not composed of pure active compound.

Hence it was an object of the present invention to produce granules of riboflavin containing no active ingredient.

We have found that this object is achieved by a process for producing riboflavin granules, which comprises compacting riboflavin powder which contains no inactive ingredient and whose mean maximum particle diameter is less than 25 μm to give strands or ribbons, and subsequently reducing the size of the latter to a mean maximum particle diameter of 50–1,000 μm.

Compaction is a conventional process used for a large number of industrial products such as chromium dioxide, fertilizers, crop protection agents and, to a small extent, pharmaceuticals. It comprises compressing a powdered product between two rolls which are rotating in opposite directions to give strands or ribbons. The rolls may be completely smooth or have recesses of defined shape. It is also possible to employ heatable or coolable rolls. Once the material has been compacted it can be broken up using screen size reducers or rough or toothed rolls and, if necessary, reduced further in size by conventional gentle processes and fractionated by subsequent screening. Dust and particles which are too large can be recycled (see, for example, R. Voigt, "Lehrbuch der pharmazeutischen Technologie", Verlag Chemie, (1975), page 163, K. H. Bauer, K. H. Frömming and C. Führer, "Pharmazeutische Technologie", Georg Thieme Verlag Stuttgart, New York, (1986), pages 367–368).

In view of the fact that riboflavin powder cannot be compressed to stable tablets, the successful use of this process in the present case was unexpected.

Pressures of from 5 to 20 kN/cm width of the roll, preferably from 7 to 13 kN/cm, are particularly advisable for the compaction of riboflavin, which is usually carried out at from 0° to 50° C., preferably at about 25° C.

The riboflavin granules according to the invention, which contain less than 15% dust (maximum particle diameter below 50 μm) can be processed further without difficulty. They are particularly advantageous for (direct) tabletting with the auxiliaries conventional for this purpose, alone or together with other active compounds. The tabletting process is also conventional, being carried out either directly or after wet granulation, so that further details are unnecessary.

The tablets obtainable in this way not only contain more than 50% by weight riboflavin but also have mechanical properties as good as those obtainable with binder-containing granules.

The granules are outstandingly suitable for producing riboflavin-containing drugs and human and animal foods. In the case of animal foods, it does not have to be highly pure but can still contain biomass derived from the preparation of the riboflavin by fermentation. In the case of human foods, the vitaminization of flour is an important area of use.

EXAMPLES A, B AND C

Riboflavin powder with a mean particle size of 20 μm was converted into ribbons in a roll compaction apparatus in three separate experiments A, B and C; the pressure was from 7 to 10 kN/cm width of the roll. The resulting ribbons were then reduced in size using a screen size reducer (630 μm mesh width).

The resulting granules had mean maximum particle diameters below 600 μm.

Details of the experiments and the properties of the granules and tablets produced therefrom are to be found in the tables which follow.

| | Riboflavin powder | Riboflavin granules | | | Comparison[2] |
|---|---|---|---|---|---|
| | | A | B[1] | C | |
| Pressure [kN/cm] | — | 8 | 7 | 10 | — |
| Particle size [μm] | 20 | <630 | <450 | <630 | — |
| Bulk density [g/cm$^{-3}$] | <0.2 | 0.53 | 0.44 | 0.51 | 0.56 |
| Dust test[3] | | | | | |
| after 0 sec | | 4 | 11 | 4 | 17 |
| 10 | | 3 | 7 | 3 | 12 |
| 30 | | 2 | 4 | 2 | 8 |
| Flowability | very poor | good | satisfactory to good | good | good |
| Electrostatic charging | high | very low | very low | very low | very low |

| | Behavior in a tablet formulation[4] | | | | |
|---|---|---|---|---|---|
| | Riboflavin powder | Riboflavin granules | | | Comparison[2] |
| | | A | B[1] | C | |
| Compression | not compressible | good | good | good | good |
| Hardness [N][5] | — | 109 | 95 | 116 | 105 |
| Disintegration [min][6] | — | 2 | 3 | 3 | 7 |
| Friability | — | 0.1 | 0.1 | 0.1 | 0.2 |

| | Behavior in a tablet formulation[4] | | | | |
|---|---|---|---|---|---|
| | Riboflavin powder | Riboflavin granules A | B[1] | C | Comparison[2] |
| [%][7] | | | | | |

[1]The fraction above 500 μm was removed by screening.
[2]The commercial comparison granules contained 95% by weight riboflavin, about 4% by weight gum arabic and a little silica gel
[3]Casella dust test. The reduction in the transmission of light in a Casella dust chamber is measured. The greater the reduction in the transmission of light, the worse is the dusting behavior of the substance.
[4]The formulation for direct tabletting comprised, per tablet,
156 mg of riboflavin granules
140 mg of lactose
  5 mg of polyvinylpyrrolidone of K value* 30
  5 mg of insoluble polyvinylpyrrolidone
  4 mg of magnesium stearate
  2 mg of silica
[5]Heberlein/Schleuninger hardness tester
[6]Tested in simulated gastric juice as specified in the European Pharmacopoeia V.5.1.1.
[7]Measured in a Roche Friabilator
*US Pharmacopeia 22, monograph on povidone, page 1118.

As is evident from the table, the riboflavin granules containing no inactive ingredient according to the invention proved to be far superior to riboflavin powder both in their technical processing properties and in tablets. Compared with commercial riboflavin granules containing inactive ingredient, the granules containing no inactive ingredient according to the invention had better results in the dust test and in the tablet disintegration, while the other properties were at least approximately equally good.

EXAMPLE D

Riboflavin powder with a mean particle size of 20 μm was passed through a roll compaction apparatus under a pressure of 10 kN/cm width of the roll as in Example C. The resulting ribbons were then reduced in size using a screen size reducer (630 μm mesh width).

The product was converted into low-dose riboflavin tablets of the following formulation to test the uniformity of content as specified in the European Pharmacopoeia (V.5.2.2.):

3 mg of riboflavin granules
7 mg of polyvinylpyrrolidone of K value 30
7 mg of insoluble polyvinylpyrrolidone
181 mg of lactose
2 mg of magnesium stearate
1 mg of silica 500 mg of this mixture were passed through a 1 mm screen, mixed in a cube mixer for 20 min and compressed to tablets with a very low pressure (4 kN) in a rotary tabletting machine.

The general properties compared with tablets produced with commercial riboflavin granules containing inactive ingredient are to be found in the table which follows.

| | Example D | Comparison[2] | Comparison[8] |
|---|---|---|---|
| Weight [mg] | 208 | 202 | 205 |
| Diameter [mm] | 8 | 8 | 8 |
| Hardness [N][5] | 97 | 108 | 100 |
| Disintegration [min][6] | 3–4 | 4 | 5 |
| Friability [%][7] | 0.1 | 0.1 | 0.1 |
| Riboflavin [%] | 1.43 | 1.40 | 1.38 |

[2]The commercial comparison granules contained 95% by weight riboflavin, about 4% by weight gum arabic and a little silica gel
[5]Heberlein/Schleuninger hardness tester
[6]Tested in simulated gastric juice as specified in the European Pharmacopoeia V.5.1.1.
[7]Measured in a Roche friabilator
[8]The commercial comparison granules contained 98% by weight riboflavin and about 2% methylcellulose.

The uniformity of the riboflavin content in 20 tablets is evident from the table which follows:

| Tablet No. | Ex. D [%] | Comparison[2] [%] | Comparison[8] [%] |
|---|---|---|---|
| 1 | 1.482 | 1.307 | 1.822 |
| 2 | 1.462 | 1.383 | — |
| 3 | 1.521 | 1.273 | 1.172 |
| 4 | 1.413 | 1.308 | 1.728* |
| 5 | 1.252 | 1.415 | 1.546 |
| 6 | 1.349 | 1.440 | 0.990* |
| 7 | 1.340 | 1.234 | 1.133 |
| 8 | 1.379 | 1.796* | 1.450 |
| 9 | 1.354 | 1.573 | 0.832* |
| 10 | 1.584 | 1.314 | 2.040* |
| 11 | 1.446 | 1.263 | 1.089 |
| 12 | 1.539 | 1.353 | 1.634 |
| 13 | 1.483 | 1.554 | 0.807* |
| 14 | 1.449 | 1.186 | 1.656 |
| 15 | 1.380 | 1.365 | 1.639 |
| 16 | 1.536 | 1.555 | 1.054 |
| 17 | 1.265 | 1.523 | 1.110 |
| 18 | 1.447 | 1.343 | 1.792* |
| 19 | 1.537 | 1.610 | 1.665 |
| 20 | 1.352 | 1.264 | 1.030* |
| Average | 1.4285 | 1.4030 | 1.3784 |
| rel. standard deviation | 0.093 | 0.155 | 0.374 |
| ± 25% of the average | 1.0714–1.7856 | 1.0522–1.7537 | 1.0338–1.7232 |

* = outside the prescribed limits

The maximum deviations from the average with the riboflavin granules containing no inactive ingredient according to the invention were +8% and −12%. The deviations were considerably larger with the commercial riboflavin granules containing inactive ingredient and in some cases even exceeded the prescribed maximum limits of ±25% (indicated by *).

EXAMPLE E

Riboflavin powder with a mean particle size of 20 μm was passed through a roll compaction apparatus under a pressure of about 0.9 kN/cm width of the roll. The resulting ribbons were then reduced in size using two screen size reducers in series (630 μm and 315 μm mesh widths).

To test the suitability for use in a conventional premix for vitaminizing flour, the resulting riboflavin granules were incorporated in the following mixture (5 l vessel with plow share mixer at 150 rpm for 30 min):

3% riboflavin granules
4% thiamine mononitrate
30% nicotinamide
2% tricalcium phosphate
25% reduced iron powder
36% corn starch As conventional in commerce, this mixture was passed through a 200 μm shaken screen in order to remove larger particles and/or agglomerates (including of riboflavin) and achieve a homogeneous distribution in the flour. An important aim is therefore to keep this residue as small as possible.

The amounts of the residue in a series of tests are compared with microcrystalline riboflavin powder in the following table:

| % riboflavin residue on a 200 μm screen based on riboflavin employed | | |
|---|---|---|
| Riboflavin powder | | Example E |
| | 3.88 | 7.70 |
| | 4.07 | 2.20 |
| | 2.76 | 1.93 |
| | 3.53 | 2.92 |
| | 3.79 | 4.18 |
| | 4.13 | |
| Average | 3.69 | 3.79 |
| rel. standard deviation | 0.461 | 2.11 |

The results show that the riboflavin granules containing no inactive ingredient according to the invention are, while having significantly better properties such as good flowability, low dusting and low electrostatic charging (see Examples A–C), at least as suitable for vitaminizing flour as is microcrystalline riboflavin powder.

We claim:

1. A process for producing pure riboflavin granules which comprises compacting riboflavin powder whose mean maximum particle diameter is below 25 μm to give strands or ribbons, and then reducing the latter to a mean maximum particle diameter of from 50 to 1,000 μm.

2. A process for producing riboflavin-containing dosage forms, which comprises compressing a composition containing pure riboflavin granules as produced in claim 1 to form a dosage form.

* * * * *